US005889869A

United States Patent [19]

Botros et al.

[11] Patent Number: 5,889,869

[45] Date of Patent: Mar. 30, 1999

[54] INVISIBLE ACOUSTIC SCREEN FOR OPEN-PLAN OFFICES AND THE LIKE

[75] Inventors: Radamis Botros, Nepean; Rafik A Goubran, Ottawa, both of Canada

[73] Assignee: Botrus Teleconferencing & Acoustics Consulting, Ltd., Nepean, Canada

[21] Appl. No.: 682,135

[22] Filed: Jul. 17, 1996

[30] Foreign Application Priority Data

Jun. 24, 1996 [CA] Canada .................................. 2179794

[51] Int. Cl.[6] ............................ H03B 29/00; A61F 11/06

[52] U.S. Cl. .................... 381/71.11; 381/71.1; 381/94.7; 364/724.19

[58] Field of Search ................................ 381/71, 94, 66, 381/71.1–71.14, 94.1–94.9, 123, 124; 379/388, 390, 406; 364/724.19

[56] References Cited

U.S. PATENT DOCUMENTS

| | | | |
|---|---|---|---|
| 4,463,222 | 7/1984 | Poradowski . | |
| 4,636,586 | 1/1987 | Schiff | 381/71.11 |
| 4,934,483 | 6/1990 | Kallergis . | |
| 5,170,433 | 12/1992 | Elliott et al. | 381/94 |
| 5,216,721 | 6/1993 | Melton | 381/71 |
| 5,216,722 | 6/1993 | Popovich | 381/94 |
| 5,289,147 | 2/1994 | Koike et al. . | |
| 5,323,459 | 6/1994 | Hirano | 391/94 |
| 5,327,496 | 7/1994 | Russell et al. | 381/71 |
| 5,381,473 | 1/1995 | Andrea et al. | 379/387 |
| 5,388,160 | 2/1995 | Hashimoto et al. | 381/71 |
| 5,406,622 | 4/1995 | Silverberg et al. | 381/94.7 |
| 5,408,532 | 4/1995 | Yokota et al. | 381/71 |
| 5,432,857 | 7/1995 | Geddes | 381/71 |
| 5,557,682 | 9/1996 | Warner et al. | 381/71 |
| 5,559,881 | 9/1996 | Sih | 379/406 |
| 5,625,684 | 4/1997 | Matouk et al. | 381/94.7 |
| 5,646,991 | 7/1997 | Sih | 379/406 |

*Primary Examiner*—Curtis A. Kuntz
*Assistant Examiner*—Xu Mei
*Attorney, Agent, or Firm*—Thomas R. Vigil

[57] ABSTRACT

The invisible acoustic screen for reducing sound leakage from handsfree telephones, loudspeaking computer terminals, and the like in a workspace includes a sound reducing apparatus comprising: a sound producing loudspeaker; a cancelling loudspeaker; a sensing microphone having an output; a delay circuit; and, an adaptive filter circuit having a value determined by a transfer function between the sound producing loudspeaker and the sensing microphone and by a transfer function between the cancelling loudspeaker and the sensing microphone; and the output of the sensing microphone being fed back to the adaptive filter circuit; and the received signal coupled through a delay circuit to the sound producing loudspeaker.

5 Claims, 7 Drawing Sheets

INVISIBLE ACOUSTIC SCREEN FOR OPEN-PLAN OFFICES AND THE LIKE

BACKGROUND OF THE INVENTION

1. Field of the Invention

The present invention is directed to acoustic noise confinement and reduction in general, and in particular to the confinement of sound to the region of use of loudspeaking or handsfree telephones, computer terminals, etc., as are commonly used in open-plan offices, cubicles, booths and so forth, particularly where the partitioning walls do not extend fully to the ceiling. By reducing the loudspeaker radiated sound beyond the edge of partitions, the noise in neighboring booths may be reduced to the leakage of the sound locally produced, such as the voice of an occupant on the telephone. Thus, noise from loudspeaking telephony becomes comparable to that from ordinary handset use.

2. Description of the Related Art

Heretofore, various noise suppressing systems have been proposed. Several examples of such previously proposed noise suppressing systems are disclosed in the following U.S. Pat. Nos.:

| U.S. Pat. No. | Patentee |
|---|---|
| 4,463,222 | Poradowski |
| 4,934,483 | Kallergis |
| 5,289,147 | Koike et al. |
| 5,381,473 | Andrea et al. |
| 5,388,160 | Hashimoto et al. |
| 5,432,857 | Geddes |
| 5,408,532 | Yokota et al. |

The Poradowski U.S. Pat. No. 4,463,222 discloses a noise cancelling transmitter for voice communication comprising a casing having a principle surface opposed to the mouth of the user and three side surfaces facing upwardly, laterally and downwardly when the principle surface is so opposed. Noise cancelling openings in the three side surfaces communicate noise to the back of a diaphragm in the transmitter microphone. Openings in the principle surface communicate both noise and the speaker's voice to the front of the diaphragm. The noise acts on both sides of the diaphragm and is thus cancelled, while the voice acts only on one side of the diaphragm and vibrates it.

The Kallergis U.S. Pat. No. 4,934,483 discloses a method of reducing the overflying noise of airplanes having a propeller driven by a piston engine. The propeller is arranged on the engine shaft in such a way that positive components of the engine sound pressure fall on negative components of the propeller sound pressure. It is preferable to use an engine/propeller combination in which the number of engine ignitions per revolution of the propeller shaft divided by the number of the propeller blades is an integer, preferably being equal to 1.

The Koike et al. U.S. Pat. No. 5,289,147 discloses an image forming apparatus which includes a housing, a mechanism, mounted in the housing, for forming images on a medium, and an operation panel formed on the housing, the mechanism being driven in accordance with operating instructions input from the operation panel by an operator. The apparatus further includes a microphone, provided in the housing, for detecting a noise generated by a driving of the mechanism, and a noise cancelling unit for outputting an acoustic wave to an area adjacent to the operation panel of the housing, the acoustic wave being generated based on the noise detected by the microphone so that the acoustic wave and a noise present in the area cancel each other out, whereby the noise present in the area is reduced.

The Andrea et al. U.S. Pat. No. 5,381,473 discloses an apparatus for reducing acoustic background noise for use with a telephone handset or a boom microphone device or the like. The apparatus includes first and second microphones which are arranged such that the first microphone receives a desired speech input and the background noise present in the vicinity of the speech, and the second microphone receives substantially only the background noise. The background noise from the second microphone is converted into a corresponding electrical signal and subtracted from a signal corresponding to the speech and background noise obtained from the first microphone so as to produce a signal representing substantially the speech.

The Hashimoto et al. U.S. Pat. No. 5,388,160 discloses a noise suppressor in which a noise signal detected by a first detector is inputted to an adaptive filter and a FIR filter. An output signal of the adaptive filter is reproduced by a speaker. The signal reproduced by the speaker and a noise signal from a noise source are detected by a second detector. The signal detected by the second detector is band-limited by a filter circuit and sent to a LMS computing circuit. The LMS computing circuit updates a coefficient of the adaptive filter so as to minimize an output signal of the filter circuit in response to an output signal of the FIR filter and an output signal of the filter circuit.

The Geddes U.S. Pat. No. 5,432,857 discloses an active muffler for use in motor vehicles comprising a sensor, an electronic control responsive to the signal generated by the sensor for producing a drive signal delivered to a transducer which emits cancellation pulses phased 180° from the sound pressure pulses passing through a conduit, where both front and rear sides of the transducer are acoustically coupled to the conduit to improve the efficiency of the transducer operation. Preferably, the acoustic coupling comprises an enclosed chamber including a port for communicating with the conduit which can be tuned to resonate at predetermined frequencies. When both sides of the transducer are so coupled to the conduit, the transducer has increased efficiency over a broad band of frequencies, and the frequency band can be broadened at the low end as required to accommodate the frequencies generated by a source of noise. A tandem transducer mounting arrangement constructed according to the teachings of this invention reduces vibration of the housing. The transducer mounting arrangement is particularly suitable for use in adapting noise cancellation techniques to replace passive mufflers on motor vehicles.

The Yokota et al. U.S. Pat. No. 5,408,532 discloses the use of an ignition pulse signal which is transformed into a single vibration noise source signal (primary source) so as to obtain a frequency spectrum composed of 0.5.times.n order components which is converted into a cancelling signal after being subjected to the sum of convolution products processed with filter coefficients of an adaptive filter. Further the cancelling signal is converted into a cancelling sound by a speaker and outputted to the passenger compartment to cancel vibration noise at a noise receiving point. The state of noise reduction is detected as an error signal by a microphone and the error signal is inputted to an exponential averaging circuit where the error signal is exponentially averaged with previous error signals by a trigger signal of the primary source from a trigger signal generating circuit. The error signal, as a result of this averaging, is compressed and then outputted to a least mean square (LMS) operational circuit. In the LMS operational circuit, the filter coefficients are updated based on the primary source inputted via speaker/microphone transmission characteristic correction circuit and the compressed error signal.

SUMMARY OF THE INVENTION

The purpose of the present invention is to upgrade the degree of acoustic privacy of loudspeaking telephony in an open-plan office to approach that of handset operation.

The present invention endeavors to apply the known teachings of sound cancellation, both fixed and pre-optimized and adaptive, primarily to the open-plan office environment. The "noise" mitigation of the present invention may be described as the creation of an invisible acoustic screen, or umbrella, thus reducing sound leakage from handsfree telephones, loudspeaking computer terminals, and the like, in an open-plan cubicle to its neighboring space.

Accordingly, the present invention provides an acoustic screen for reducing sound leakage from handsfree telephones, loudspeaking computer terminals, and the like in a workspace comprising an apparatus for reduction of sound leakage from a loudspeaker operated in a particularly confined space. The acoustic screen includes a sound reducing apparatus comprising: a sound producing loudspeaker; a cancelling loudspeaker; a sensing microphone having an output; a delay circuit; and, an adaptive filter circuit having a value determined by a transfer function between the sound producing loudspeaker and the sensing microphone and by a transfer function between the cancelling loudspeaker and the sensing microphone; and, the output of the sensing microphone being coupled through the delay circuit to the sound producing loudspeaker and through the adaptive filter to the cancelling loudspeaker.

DESCRIPTION OF THE PREFERRED EMBODIMENT(S)

Figure 1:
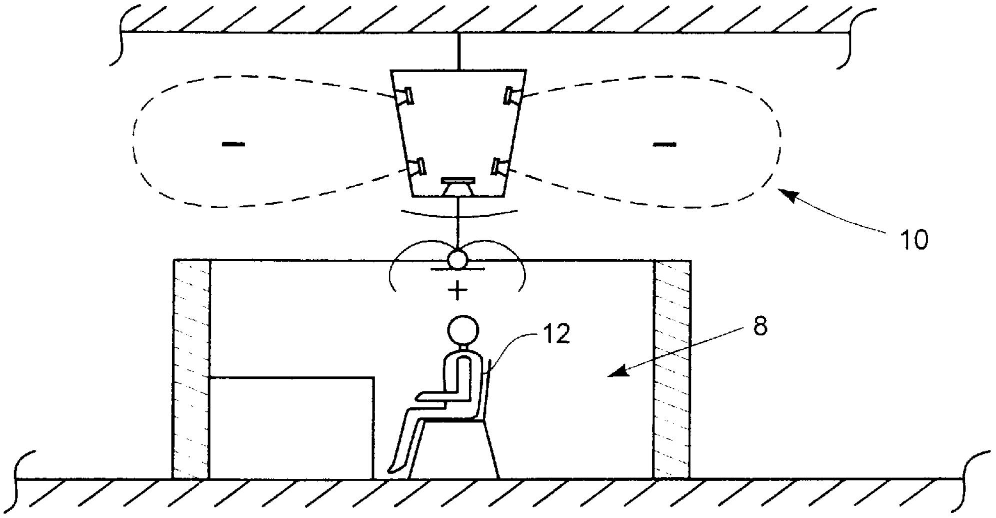
FIG. 1 is an elevational view of an open-plan office, booth or cubicle, having sound leakage reduction apparatus constructed according to the teachings of the present invention suspended above the occupant of the cubicle.

Referring now to FIG. 1 in greater detail, there is illustrated therein, an elevational view of an open-plan office, booth or cubicle 8, having sound leakage reduction apparatus 10 constructed according to the teachings of the present invention suspended above an occupant 12 of the cubicle.

Figure 2:
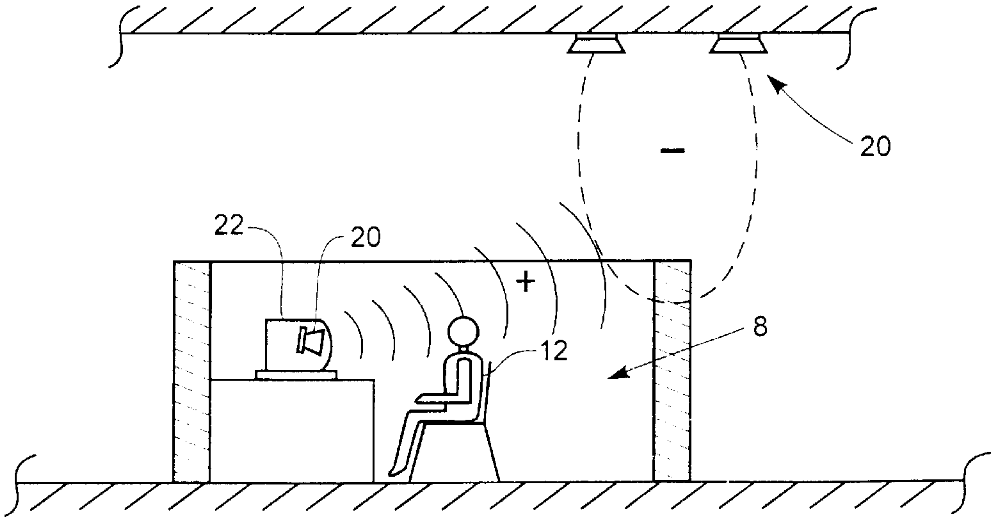
FIG. 2 is an elevational view of a modification of the apparatus shown in FIG. 1 and shows a sound producing loud speaker of the apparatus positioned in front of the occupant.

FIG. 2 illustrates an elevational view of a modification of the apparatus 10 shown in FIG. 1 and shows a sound producing loud speaker 20 of an apparatus 22 positioned in front of the occupant 12.

Figure 3:
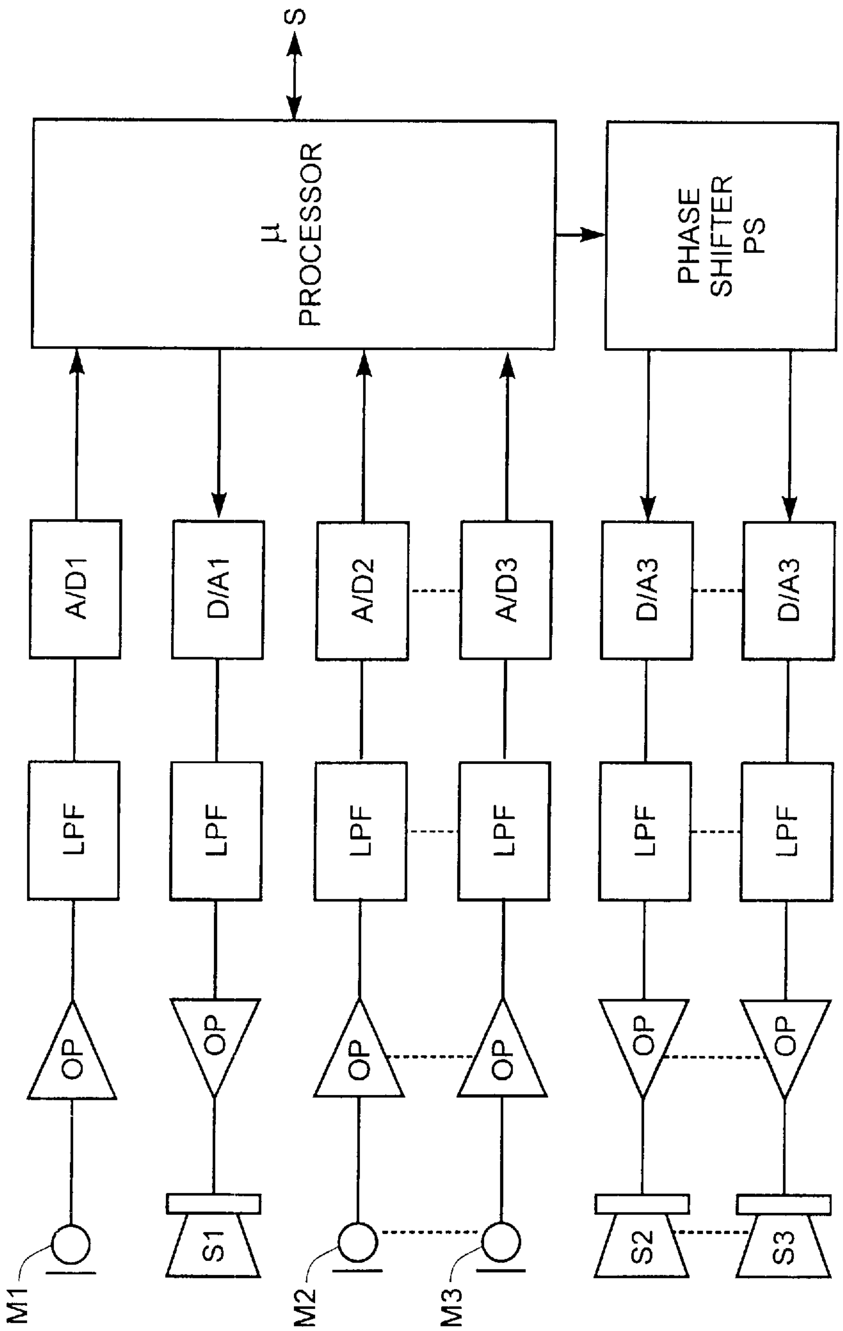
FIG. 3 is a high level block schematic circuit diagram of a circuit suitable for use in the sound leakage reduction apparatus shown in FIG. 1.

FIG. 3 illustrates a high level block schematic circuit diagram of a circuit suitable for use in the sound leakage reduction apparatus shown in FIG. 1 and includes three microphones M1, M2 and M3, three speakers S1, S2 and S3, six operational amplifiers OP, six low pass filters LPF, three analog-to-digital conversion circuits A/D1, A/D2 and A/D3, three digital-to-analog conversion circuits D/A1, D/A2 and D/A3, a microprocessor and a phase shifting circuit PS connected together in the manner shown in FIG. 3.

Figure 4:
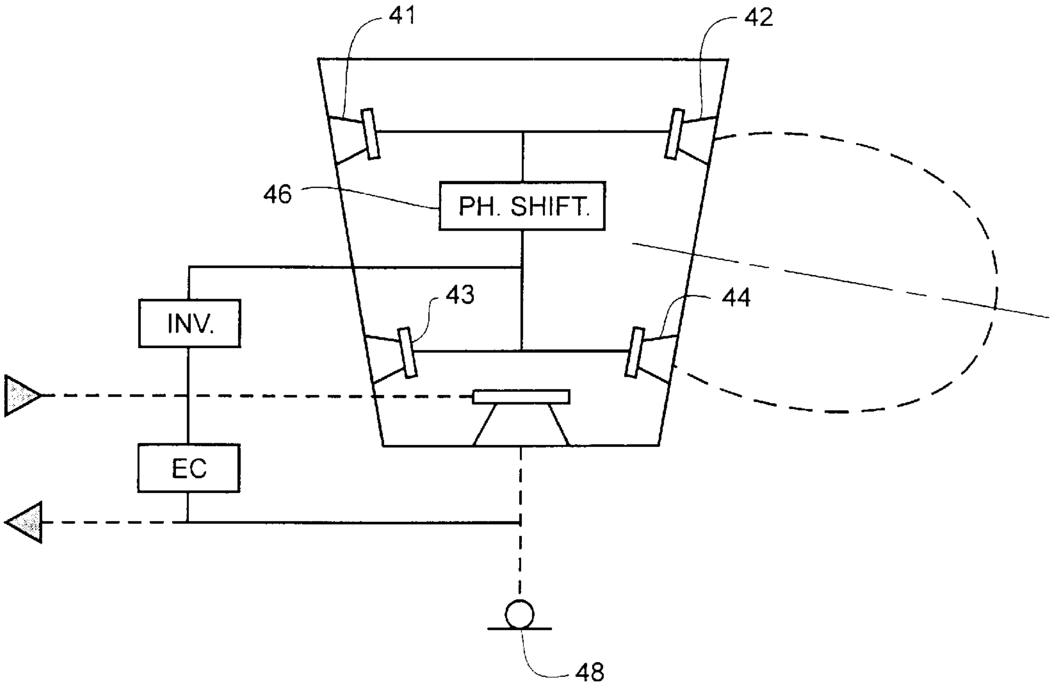
FIG. 4 is a block schematic diagram of the apparatus shown in FIG. 1.

FIG. 4 illustrates a block schematic diagram of the apparatus shown in FIG. 1 which includes four speakers 41–44, a phase shift circuit 46 and a sensing microphone 48 connected as shown.

Figure 5:
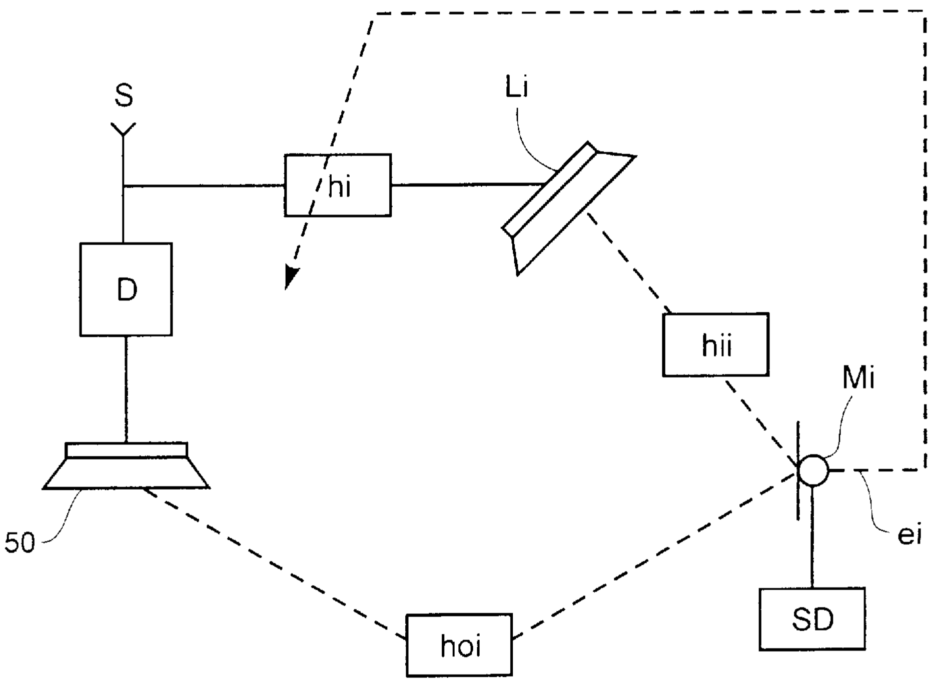
FIG. 5 is a block diagram of the DSP algorithm used for each cancelling loudspeaker system.

FIG. 5 is a block diagram of a DSP algorithm which is used for each of the cancelling loudspeaker systems. In this algorithm: h0i represents the transfer function between a sound producing loudspeaker 50 and a sensing microphone Mi; hii represents the transfer function between a cancelling loudspeaker Li and the sensing microphone Mi having an output ei; and, hi is an adaptive finite impulse response filter implemented inside the DSP system between the received signal S and the cancelling loudspeaker Li. A delay circuit D is introduced by the DSP system to ensure the causality of the adaptive filter hi. See the DPS algorithm in FIG. 5 and the block diagram of the adaptive FIR filter shown in FIG. 6.

Figure 7:
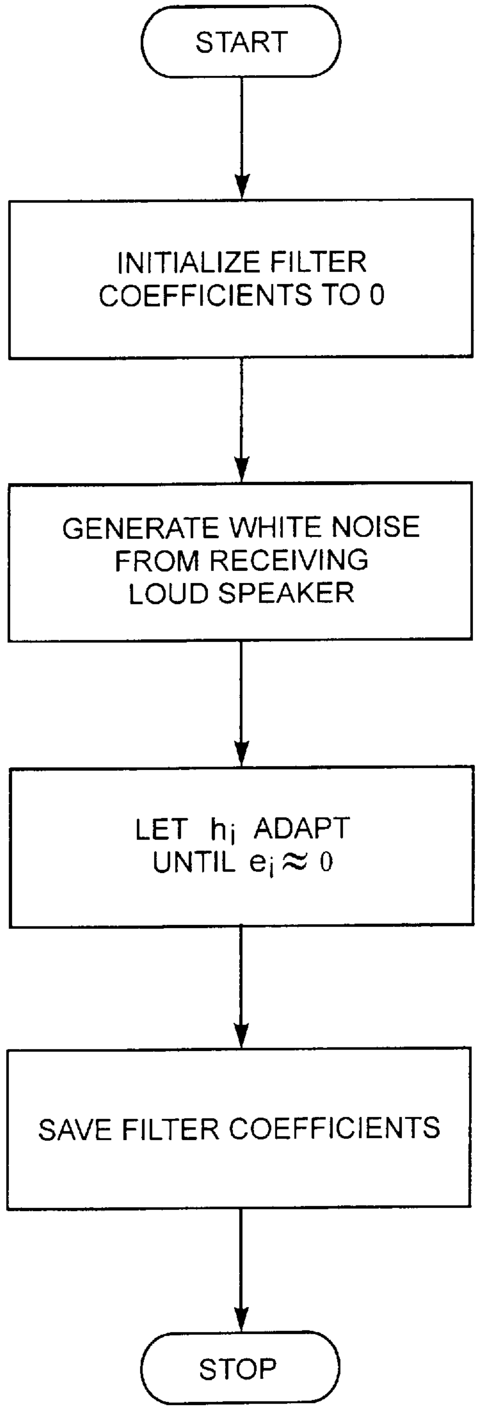
FIG. 7 is a flow chart of a calibration procedure followed in setting-up the sound leakage reduction apparatus shown in FIG. 1.

During a calibration procedure, the transfer functions h0i and hii are measured by the DSP system. This is done by sending, sequentially, a known signal from each loudspeaker, acquiring the corresponding signal from the sensing microphone Mi, and analyzing it. See the flow chart in FIG. 7.

If the room is completely static, hi can be chosen such that the error signal ei at the microphone Mi is zero:

$$ei=S\ D\ h0i+S\ hi\ hii=0$$

which leads to:

$$hi=-D\ h0i/hii.$$

D should be chosen as the minimum delay which ensures that the adaptive filter hi is causal.

Figure 8:
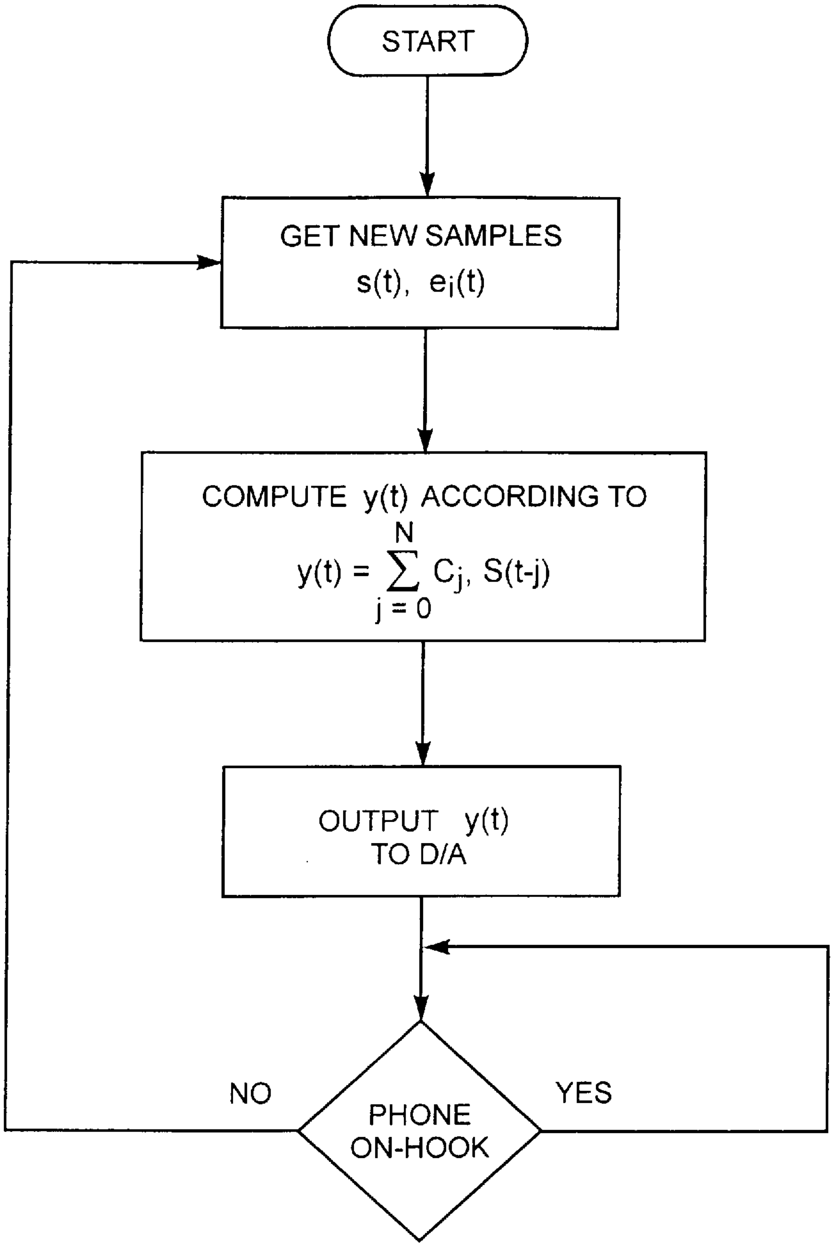
FIG. 8 is a flow chart of the procedure or protocol followed by the microprocessor of the sound leakage reduction apparatus in the normal operation of the apparatus.

However, in practice, the transfer functions h0i and hii change when people move in the surrounding area, which implies that the adaptive filter hi has to be implemented. The size of the adaptive filter hi, its initial coefficients, and the delay value of D are determined during the calibration procedure. The coefficients are then adapted using an LMS adaptation algorithm in subbands to minimize the error signal ei. See the flow chart shown in FIG. 8. Such an adaptive algorithm is described in *ADAPTIVE FILTER THEORY*, by Simon Haykin, Prentice-Hall, Inc., Upper Saddle River, N.J., 1996. See Chapter 9, Least-Mean-Square Algorithm, Section 9.11, Normalized LMS Algorithm, the disclosure of which is incorporated herein by reference. The filter is only adapted during the silence intervals. The adaptation is frozen as soon as near-end speech is detected using a speech detector SD connected to the transmitting sensing microphone.

The same blocks and algorithms are repeated for each pair of cancelling loudspeaker system and cancelling/sensing microphone. Since the value of the delay circuit D is a common value for all of them, the maximum value should be the one used. The interaction between the various cancelling loudspeaker system is taken care of by the adaptive filter hi.

Figure 6:
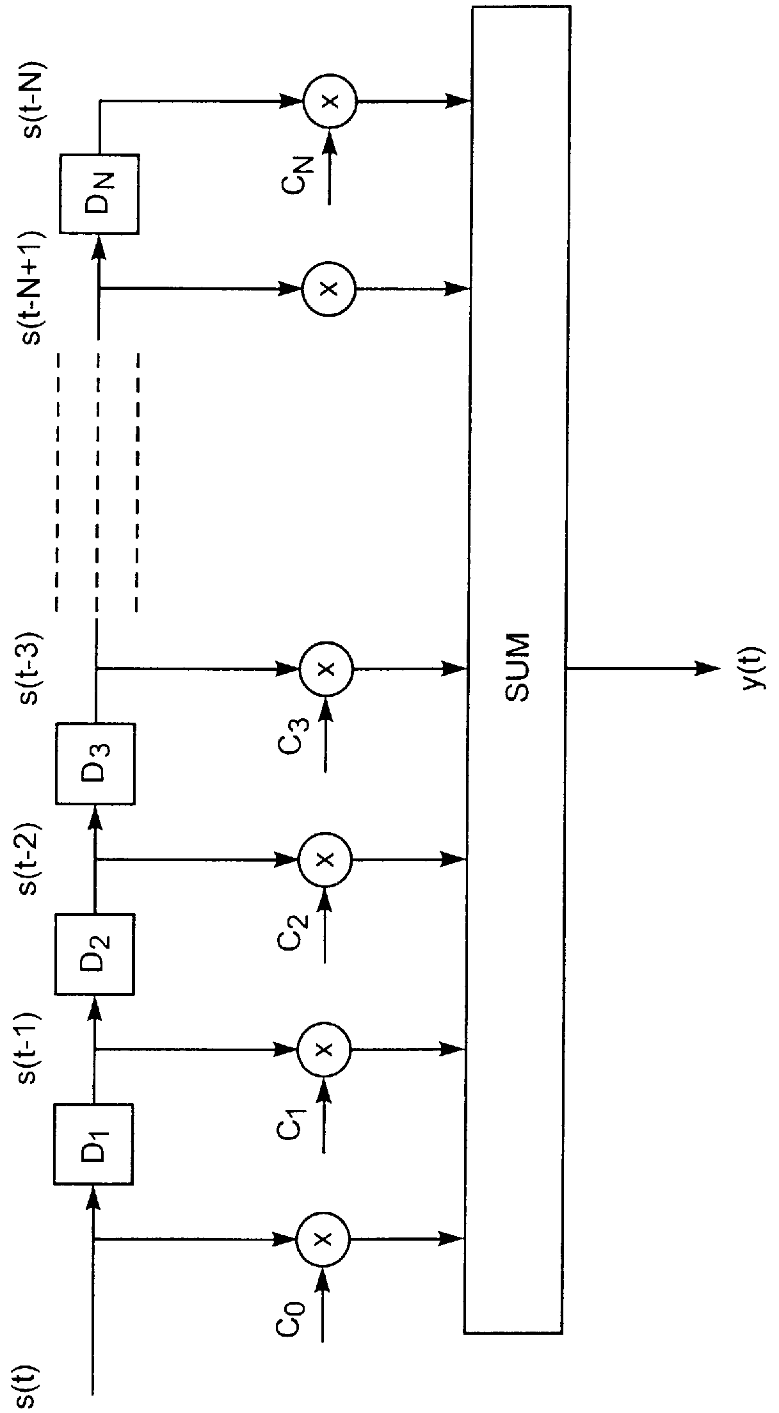
FIG. 6 is a block schematic diagram of an adaptive FIR filter, hi.

A block diagram of an adaptive FIR filter hi is shown in FIG. 6. Here, $$y(t) = \sum_{j=0}^{n} C_j S(t-j)$$

where:

S(t) is the received signal (Filter Input);

y(t) is the signal feeding the cancelling loudspeaker (Filter Output); and $C_j$ are the filter coefficients.

From the foregoing description, it will be apparent that the acoustic screen of the present invention has a number of advantages, some of which have been described above and others of which are inherent in the invention. Also it will be understood that modifications can be made to the acoustic screen described above without departing from the teachings of the present invention. Accordingly, the scope of the invention is only to be limited as necessitated by the accompanying claims.

We claim:

1. An acoustic screen for reducing sound leakage from handsfree telephones, loudspeaking computer terminals, and the like in a workspace including a sound leakage reducing apparatus, comprising:

a sound producing loudspeaker;

a canceling loudspeaker;

a sensing microphone having an output;

a delay circuit;

an adaptive filter circuit having a value determined by a transfer function between said sound producing loudspeaker and said sensing microphone, and by a transfer function between said canceling loudspeaker and said sensing microphone;

said output of said sensing microphone being coupled through said delay circuit to said sound producing loudspeaker and through said adaptive filter to said canceling loudspeaker;

said adaptation being frozen as soon as near end speech is detected using a speech detector connected to the transmitting sensing microphone; and the value of the adaptive filter hi is chosen such that an error signal ei at the sensing microphone is zero with $$ei = S \times D \times h0i + S \times hi \times hii = 0$$

where:

S is the output signal from said sensing microphone;

D is the delay value of the delay circuit;

h0i is the transfer function between said sound producing loudspeaker and said sensing microphone;

hi is the value of the adaptive filter;

hii is the transfer function between said canceling loudspeaker and said sensing microphone;

which leads to:

$$hi = -D \times (h0i/hii).$$

2. The apparatus of claim 1, wherein the value of the delay circuit is chosen as the minimum delay which ensures that the adaptive filter is causal.

3. The apparatus of claim 1, wherein the value of the coefficients of the adaptive filter are determined using an LMS adaptation algorithm in subbands to minimize the error signal.

4. The apparatus of claim 1, wherein the value of the adaptive filter is defined as follows:

$$y(t) = \sum_{j=0}^{n} C_j S(t-j)$$

Where:

S(t) is the received signal;

y(t) is the signal feeding the canceling loudspeaker; and $C_j$ are the filter coefficients.

5. The apparatus of claim 1, wherein the canceling loudspeaker comprises a plurality of cooperating loudspeakers.

* * * * *

UNITED STATES PATENT AND TRADEMARK OFFICE
CERTIFICATE OF CORRECTION

PATENT NO. : 5,889,869
DATED : March 30, 1999
INVENTOR(S) : Radamis Botrus, et. al.

It is certified that error appears in the above-identified patent and that said Letters Patent is hereby corrected as shown below:

Column 6, Claim 4, line 37 after "signal" insert --(filter input)--

Column 6, Claim 4, line 38 after "loudspeaker" insert --(filter output)--.

Signed and Sealed this

Eighth Day of February, 2000

Attest:

Q. TODD DICKINSON

*Attesting Officer* *Commissioner of Patents and Trademarks*